United States Patent [19]
Lawlis, Jr. et al.

[11] Patent Number: 5,801,034
[45] Date of Patent: *Sep. 1, 1998

[54] METHOD FOR KILLING CELLS WITHOUT LYSIS AND ENZYME RECOVERY

[75] Inventors: Virgil B. Lawlis, Jr., San Mateo; Henry G. Heinsohn, Pacifica; Enrique F. Baliu, San Francisco, all of Calif.

[73] Assignee: Genencor International, Rochester, N.Y.

[*] Notice: The term of this patent shall not extend beyond the expiration date of Pat. No. 5,378,621.

[21] Appl. No.: 356,042

[22] Filed: Dec. 14, 1994

Related U.S. Application Data

[63] Continuation of Ser. No. 128,565, Sep. 29, 1993, abandoned, which is a continuation of Ser. No. 807,475, Dec. 13, 1991, abandoned, which is a continuation-in-part of Ser. No. 799,864, Nov. 27, 1991, abandoned, which is a continuation of Ser. No. 365,945, Jun. 13, 1989, abandoned.

[51] Int. Cl.$^6$ .................... C12N 9/00; C12P 21/00
[52] U.S. Cl. .................. 435/183; 435/171; 435/71.1; 435/814; 435/911; 435/917; 435/942; 435/256.8; 435/254.1; 435/244; 530/412; 530/823; 530/824; 424/605
[58] Field of Search .................... 424/605; 435/243, 435/171, 71.1, 244, 814, 511, 252.1, 256.85, 254.1, 259, 824, 823, 260, 261

[56] References Cited

U.S. PATENT DOCUMENTS

| | | | |
|---|---|---|---|
| 785,733 | 3/1905 | Hess | 435/259 |
| 785,734 | 3/1905 | Hess | 435/259 |
| 1,908,225 | 5/1933 | Currie et al. | 435/823 X |
| 3,134,723 | 5/1964 | Corman | 435/823 X |
| 3,345,268 | 10/1967 | Corman | 435/814 X |
| 3,459,554 | 8/1969 | Hashimoto . | |
| 3,658,650 | 4/1972 | Okazaki | 435/206 |
| 3,682,778 | 8/1972 | Kawai et al. . | |
| 3,716,452 | 2/1973 | Kitamura et al. | 435/206 |
| 3,799,868 | 3/1974 | Nikolaev et al. | 435/823 X |
| 3,816,260 | 6/1974 | Sugiyama | 195/62 |
| 3,885,050 | 5/1975 | Ridgway, Jr. et al. | 426/60 |
| 3,890,198 | 6/1975 | Kobayashi et al. | 195/66 R |
| 3,917,510 | 11/1975 | Kitamura et al. | 195/2 |
| 3,961,080 | 6/1976 | Sugimoto et al. | 426/60 |
| 4,299,858 | 11/1981 | Aubert et al. | 426/656 |
| 4,416,987 | 11/1983 | Cabane et al. | 435/71.2 |
| 4,596,778 | 6/1986 | Hitzman | 435/253 |
| 4,601,986 | 7/1986 | Wegner et al. | 435/255 |
| 4,647,458 | 3/1987 | Ueno et al. | 424/605 |
| 4,654,306 | 3/1987 | Entani et al. | 435/823 X |
| 4,725,544 | 2/1988 | Tan et al. | 435/814 X |
| 4,935,360 | 6/1990 | Klemps et al. | 435/823 X |
| 5,155,040 | 10/1992 | Kula et al. | 435/183 X |
| 5,215,908 | 6/1993 | Heinsohn et al. | 435/226 |

FOREIGN PATENT DOCUMENTS

| 0148709 | 7/1985 | European Pat. Off. . |
|---|---|---|

OTHER PUBLICATIONS

Rusul et al., "Growth and Aflatoxin Production by *Aspergillus parasiticus* NRRL 2999 in the Presence of Acetic or Propionic Acid and at Different Initial pH Values," *J. of Food Protection*, vol. 50, pp. 909–914, 919 (1987).
Kirby et al., "Further Studies on the Growth of Bread Molds as Influenced by Acidity," *Cereal Chem.*, vol. 14, pp. 865–878 (1937).
Doores, S., "Organic Acids" in A.L. Branen and M.P. Davidson (eds.) *Antimicrobials in Foods*, pp. 75–108 (1983).
Hentges, D.J., "Influence of pH on the Inhibitory Activity of Formic and Acetic Acids for Shigella," *J. of Bacteriol.*, vol. 93, pp. 2029–2030 (1967).
Scopes, R.K., *Protein Purification, Principles and Practice, Second Edition*, Springer–Verlag. pp. 55–62 (1987).
*Biochemistry* (Second Edition) The Molecular Basis of Cell Structure and Function, by Albert L. Lehninger, the Johns Hopkins University School of Medicine, Worth Publishers, Inc., Copyright 1970, 1975, pp. 162–163.
*Introduction to Fungi* (Second Edition), by John Webster, Cambridge University Press, Cambridge, Massachusetts, Copyright 1970, 1980, pp. 57–60, 97, 248–249, 264–265.
"The Cell Wall and Protein Secretion in Fungi" by Joseph G.H. Wessels. In *Proceedings of the EMBO—Alko Workshop on Molecular Biology of Filamentous Fungi, Helsinki 1989*, ed. by H. Nevalainen and M. Penttila, Foundation for Biotechnical and Industrial Fermentation Research 6 (1989): 177–186.
Crueger et al. "Biotechnology," p. 49, 1990.
Handbook of Chemistry and Physics, pp. D–120—D–121, 1970.

*Primary Examiner*—Irene Marx
*Attorney, Agent, or Firm*—Kirsten A. Anderson

[57] ABSTRACT

This invention provides a method for killing cells in fermentation mixtures in order to prepare the fermentation mixture for processing to recover or extract a desired product from the fermentation mixture. A preferred method of this invention comprises in either order, adjusting the pH of the fermentation mixture to a value equal to or less than about two pH units below the $pK_a$ of the compatible organic acid using a mineral acid, and adding a sufficient amount of a compatible organic acid and/or organic acid salt to the mixture to effect a substantially complete cell kill. The method of this invention is useful for killing microorganisms such as yeast, bacteria or fungi in any culture or fermentation mixture and is particularly useful in systems where it is desired to kill the cells without lysing them.

7 Claims, No Drawings

METHOD FOR KILLING CELLS WITHOUT LYSIS AND ENZYME RECOVERY

This is a continuation of application Ser. No. 08/128,565 filed Sep. 29, 1993, now abandoned, which is a continuation of U.S. Ser. No. 07/807,475, filed Dec. 13, 1991, now abandoned, which is a continuation-in-part of U.S. Ser. No. 07/799,864, filed Nov. 27, 1991, now abandoned, which is a continuation of U.S. Ser. No. 07/365,945, file Jun. 13, 1989, now abandoned.

FIELD OF THE INVENTION

This invention relates to the killing of yeast, bacterial or fungal cells without lysis in a culture.

BACKGROUND OF THE INVENTION

In the various processes of culturing or fermenting microorganisms, it is sometimes necessary during or at the conclusion of the fermentation process to be able to kill the active cells in the mixture so that the desired product can be recovered from the culture or fermentation mixture. This is particularly true when microorganisms containing recombinant DNA are grown as production hosts and it is desirable to prevent any viable recombinant organisms from being released into the environment. Even if the microorganisms do not contain recombinant DNA, it is often desirable to kill the microorganism prior to processing in order to ensure that viable cells are not released to the environment either in the product or in the waste products of the process.

Sometimes it is also desirable to lyse the cells at the time the cells are killed in order to recover any desired product which is produced intracellularly. One conventional way that cells are killed and lysed is by the use of heat. U.S. Pat. No. 4,601,986 to Wegner, et al. is an example of the use of heat to kill the cells and stop the growth of microorganism cultures. Another method useful on certain microorganisms is to change the osmotic pressure which causes the cells to lyse. An example of this method is illustrated in U.S. Pat. No. 4,299,858 to Aubert, et al. Another conventional method used for lysing cells is by the introduction of enzymes which break down the cell walls or membranes. Examples of this method are disclosed in U.S. Pat. No. 3,816,260 to Sugiyama, U.S. Pat. No. 3,890,198 to Kobayashi, et al. and U.S. Pat. No. 3,917,510 to Kitamura, et al. The disclosures of the above patents are incorporated herein by reference.

However, in other instances it is desirable to simply kill the microorganisms without lysing the cells. This is particularly true in systems where the cells manufacture and secrete the desired product extracellularly because lysing the cells releases additional cell debris and materials into the medium, thus making recovery and purification of the desired secreted product more difficult and costly. Therefore, when the cells in such a system can be killed without lysing them, process efficiencies in recovery and purification of the secreted products are recognized.

In addition, many conventional methods required to kill the microorganism, such as heat, are too severe and will destroy or alter the desired secreted product before the cells are killed. Previously, in this case the product must be recovered without killing the cells, which requires the use of tedious and costly containment procedures and equipment.

In large scale commercial fermentation processes, it is desirable to have efficient methods for killing the cells without lysing the cells so the resulting fermentation mixture can be processed to extract and recover the desired product being produced without maintaining the culture in containment. The heat method and other known methods for killing cells are too slow and energy inefficient for commercial use and often result in unwanted lysing of the cells. In addition, many of the conventional methods for killing cells are not compatible with culture and fermentation processes for microbial production of enzymes. Conventional methods frequently denature or alter the desired enzyme before it can be isolated and recovered, or those methods introduce materials, e.g., other enzymes, into the fermentation mixture which make the isolation, recovery and purification of the desired enzyme product more, difficult, less efficient and, consequently, more expensive.

It is, therefore, an object of this invention to provide a faster, more efficient method for substantially killing cells. It is a further object of this invention to facilitate the extraction and processing of enzyme products found in a fermentation or culture mixture or medium. It is still a further object of this invention to provide a method for effecting a substantially complete cell kill which is compatible with the microbial production of enzymes and the recovery and purification of such microbially produced enzymes.

SUMMARY OF THE INVENTION

In a preferred aspect, this invention is a method for killing microorganisms in a culture wherein said microorganisms are selected from the group consisting of yeast, bacteria and fungi which method comprises the steps of selecting a compatible organic acid having 1 to 5 carbon atoms or a compatible salt thereof, and then in either order;
 (i) adjusting the pH of the culture to a value equal to or less than about 2 pH units below the $pK_a$ of the selected compatible organic acid and/or salt thereof; and
 (ii) adding a sufficient amount of the selected compatible organic acid and/or salt to effect a substantially complete kill of the microorganism in the culture.

In another preferred aspect, this invention is a method for substantially completely killing microorganisms in a culture wherein said microorganisms are selected from the group consisting of yeast, bacterium or fungi which method comprises the steps, in either order, of (a) adjusting the pH of the culture containing the yeast, bacterium or fungi to about 2.75 or less; and (b) adding sufficient acetic acid to the culture to effect a substantially complete kill of the microorganisms in the culture.

In another aspect this invention is an aqueous composition comprising a culture of microorganisms, a sufficient amount of mineral acid to lower the pH of the composition to a value equal to or less than about 2 pH units below the $pK_a$ of a preselected compatible organic acid, and a sufficient amount of the organic acid or a salt thereof to effect a substantially complete kill of the microorganisms.

DESCRIPTION OF THE INVENTION

In the development of this invention, it has been found that the change in pH alone of a fermentation mixture does not accomplish a complete or substantially complete cell kill. For example, in a culture of *Asperaillus niger* for the production of chymosin, reducing the pH to about 2 using sulfuric acid does not accomplish a complete or substantially complete cell kill. Therefore, it has been necessary in the past to heat the fermentation mixture to sufficiently kill the cells in order to prepare the mixture for recovery of the chymosin product.

In general, in large scale commercial fermentation processes it is desirable to have a method for killing the cells in order to eliminate the presence of live cells in the final product or in the waste products produced by the process. The presence of microorganisms in the final product may generate impurities in the product or reduce the shelf-life of the enzyme products produced by the microorganism. Additionally, in the production of products from cells dangerous to humans, there may be a need to kill the cells so that they will not replicate if still existing in the product or the waste products.

As used herein, the following terms have the following meanings. The terms "microorganism" or "cell" means a single bacteria, fungi or yeast. The term "culture" refers to a number of microorganisms, for example in a fermentation broth.

The term "substantially complete kill" means that the number of viable microorganisms in a culture has been decreased by at least 4 logs. For example, if the culture originally contained $1 \times 10^8$ viable cells/ml, after treatment the culture would contain $1 \times 10^4$ viable cells/ml. More preferably, the term "substantially complete kill" means the number of viable microorganisms in the culture has been decreased by at least 6 logs. For example, if the culture originally contained $1 \times 10^8$ viable cells/ml, after treatment the culture would contain $1 \times 10^2$ viable cells/ml.

The term "complete kill" means that all of the microorganisms in the culture are no longer viable.

The "organic acid" employed to effect a substantially complete kill can be any suitable and compatible acid having 1 to about 5 carbon atoms. The organic acid selected should be one which is compatible with and is not destructive of the desired product being produced in the culture or fermentation mixture. The organic acid is "compatible" if it does not denature the desired product and does not interfere with the separation, recovery and purification methods used to recover the desired product from the mixture.

In general a sufficient amount of the organic acid is that amount required to effect a substantially complete kill of the microorganisms in the culture. More preferably a sufficient amount of a compatible organic acid will be 0.5% to about 10% by weight, preferably between about 0.75% and 5% by weight, more preferably between about 1% and 3% by weight.

The concentration of the organic acid is not critical, but should be of a high enough concentration so that the cell mixture is not excessively diluted when the organic acid is added. For example, when acetic acid is used, glacial acetic acid is a convenient form.

The process of this invention can be employed using any desired organic acid following the above steps, provided the pH of the culture or fermentation mixture is first adjusted using a mineral acid to a pH approximately equal to or less than about 2 pH units below the $pK_a$ of the organic acid selected for use for the cell kill. For example, if formic acid ($pK_a$=3.75) is to be used to accomplish the cell kill, the pH of the mixture will be adjusted with a mineral acid to about 1.75 or less, then formic acid is added to accomplish the cell kill. If propionic acid ($pK_a$=4.87) is selected for use, the pH will be adjusted to about 2.87 or less, then the propionic acid added to the mixture. After the pH is adjusted to the proper level, the organic acid is added in an amount sufficient to effect the desired cell kill.

It has also been found that it is not necessary to adjust the pH of the mixture before adding the organic acid. The organic acid can be added to the mixture, then the mineral acid added to adjust the pH to the preferred level for practice of this invention. As mentioned below, the same is true for use of the salt of the organic acid. The salt may be added, then the pH adjusted. In its broad aspect, it is merely important in the practice of this invention to have the organic acid or salt thereof present in a mixture which has a pH at or below a value which is equal to or less than about two pH units below the $pK_a$ value of the organic acid selected for use.

While not limited to or necessarily based on the following theory, it is believed that this invention achieves the unexpectedly efficient and substantially complete cell kill by the following mechanism. By reducing the pH of the mixture or media to a value equal to or less than two pH units below the $pK_a$ of the organic acid to be used, the acid is 99% protonated or uncharged and becomes "invisible" to the cell as an acid. The cell may then take up or import the neutral acid compound in the usual manner as a nutrient, because the cell does not see the compound as an acid. Once inside the cell, the acid is reionized and then alters the pH within the cell which kills the cell. Following this theory of the mechanism, it is apparently desirable to select an organic acid that the cell will be likely to take in as a nutrient in the acid's protonated form.

On the other hand, use of an acid at or near its $pK_a$ would provide greatly reduced amounts of the protonated form of the acid resulting in a substantially less efficient process.

It will also be recognized by those skilled in the art that salts of the organic acids may be used as well. For example, instead of acetic acid, sodium acetate may be used to form acetic acid in situ. The acid salt, at least about 99% thereof, will become protonated in the solution where the pH has been lowered by the mineral acid to a value equal to or less than two pH units below the $pK_a$ of the organic acid. As will also be apparent to one skilled in the art, the pH adjustment of the solution will be different when an acid salt is used than when the acid itself is used, because the salt will not affect the pH, as will the organic acid. Any organic acid salt may be used which is compatible with the solution and the components of the solution which are to be recovered from the solution after the cell kill is effected. As mentioned above, the pH of the mixture may be adjusted to a value equal to or less than about 2 pH units below the acid $pK_a$ value before or after the organic acid or salt thereof is added to the mixture. However, as a preferred practice of this invention, the pH is first adjusted to the desired value with a mineral acid, then the organic acid is added.

A preferred acid is acetic acid because it is effective with a wide range of cells and because it is one of the lowest cost acids available. Other effective acids can be used depending on the cell cultures involved and the economics of the process.

In a preferred embodiment of this invention it has been found that acetic acid is particularly useful in killing cells in fermentation processes, provided that the pH of the fermentation mixture is first adjusted to about 2.79 or less and preferably to about 2.75 or below by the addition of a mineral acid such as sulfuric acid, then the acetic acid is added. It has surprisingly been found that when this method is used the amount of acetic acid which is needed to accomplish substantially complete killing of the cells in the fermentation mixture is relatively small. In general, a substantially complete cell kill will be obtained by this method with only about 1 to 2% by weight of acetic acid. In some culture or fermentation mixtures, it may be necessary to use higher amounts of acetic acid such as about 10% or more by weight based upon the total weight of the mixture, while in other processes a substantially complete cell kill may be obtained using as little as 0.25% by weight of acetic acid. In general, however, it has been found that the amount of acetic acid added after the adjustment of the pH of the mixture will be between about 0.5% to about 10% by weight, preferably between about 0.75% and 5% by weight, more preferably between about 1% and 3% by weight.

Accordingly, another embodiment of this invention which employs acetic acid relates to a method for effecting a complete cell kill of microorganisms in a growth, culture or fermentation medium wherein said microorganisms are selected from the group consisting of yeast, bacteria and fungi which method comprises the steps in either order of:
(a) adjusting the pH of the medium to a value equal to or less than 2.79, and
(b) adding a sufficient amount of acetic acid or a salt thereof to effect a complete kill of the microorganisms in the medium.

The mineral acids that can be used to adjust the $pK_a$ of the mixtures according to the method of this invention include sulfuric acid, hydrochloric acid and other mineral acids capable of reducing the pH of the cell mixture to a value equal to or less than two pH units below the $pK_a$ of the selected compatible organic acid to be used to kill the cells in the mixture. It is desirable to select a mineral acid for adjustment of the pH which is compatible with the methods and equipment to be used to separate or extract the desired product from the fermentation or culture mixture or media. In general, it has been found that the amount of mineral acid added to adjust the pH of the mixture will be between 0.5% to about 10% by weight, preferably between about 0.75% and 5% by weight, more preferably between about 1% and 3% by weight. In some culture or fermentation mixtures, it may be necessary to use higher amounts of mineral acid. The concentration of the mineral acid used should be high enough so that the pH of the cell mixture can be adjusted to the desired level without unduly diluting the mixture.

Having described in general aspects of this invention, the invention is now illustrated by the specific embodiments described in the following examples.

EXAMPLES

In the following examples, the samples were obtained from the fermentation of an *Aspergillus niger var. awamori* typically run with 6% or 10% soy meal/glucose and harvested after 4 to 5 days. For purposes of testing the cell kill provided by this invention, particular cell production techniques are not important. The following comparative results illustrate various embodiments of this invention using a standard serial dilution test to determine the quantity of living cells remaining after the cell kill is effected. After the cell kill treatment, the samples were brought to pH 5.5, were serially diluted in 0.85% NaCl, spread plated on CMA [20 g/l Dextrose (J. T. Baker, Phillipsburg, N.J.), 20 g/l Difco Malt Extract, 1 g/l Bacto Peptone (Difco), 20 g/l Bacto Agar (Difco, Detroit, Mich.)] plates, incubated at 37 degrees Celsius for 72 hours and reported in colony forming units (CFU)/ml.

Example I

This example illustrates the effectiveness of the method of this invention in producing a substantially complete cell kill of *A. niger var. awamori*.

Two samples of an *A. niger var. awamori* fermentation mixture were adjusted to pH 2.0 with sulfuric acid. After the acid was well mixed, 4% by volume of glacial acetic acid was added to one sample. Both samples were stored overnight in a cold room then tested for cell kill. The serial dilution test results were as follows:

| S | Acetic Acid | $10^{-9}$ | $10^{-8}$ | $10^{-7}$ | $10^{-6}$ | $10^{-5}$ | $10^{-4}$ | $10^{-3}$ | $10^{-2}$ | $10^{-1}$ |
|---|---|---|---|---|---|---|---|---|---|---|
| A | 0 | 0 | 0 | 0 | 0 | 0 | 0 | 3 | 72 | TNTC |
| B | 4% (vol) | 0 | 0 | 0 | 0 | 0 | 0 | 0 | 0 | 0 |

S = Sample
TNTC means the cell growth cultures were too numerous to count.

This example shows that the sulfuric acid alone did not effect a substantially complete cell kill, whereas the combination of the sulfuric acid and acetic acid did effect a substantially complete cell kill.

Example II

In this example a portion of a fermentation mixture similar to that of Example I was cooled to 12° C. and held for 60 hours. Three examples were taken from the mixture: one was untreated and one was treated with $H_2SO_4$ alone to pH 2.0. The third sample was treated with $H_2SO_4$ to pH 2.0, glacial acetic acid was added in the amount of 1% of the weight of the mixture sample then the mixture was aerated and agitated for approximately one hour. All three samples were adjusted to pH 5.5, with NaOH, serially diluted, plated and incubated for five days at 37° C. The test results were as follows:

| Sample | $10^{-4}$ | $10^{-3}$ | $10^{-2}$ | .1 ml | 1 ml |
|---|---|---|---|---|---|
| No treatment | 30 | TNTC | TNTC | TNTC | TNTC |
| $H_2SO_4$ only (pH 2.0) | 0 | 0 | 0 | 2 | 19 |
| $H_2SO_4$ (pH 2.0)/1% acetic acid | 0 | 0 | 0 | 0 | 0 |

This example indicates that the acetic acid/sulfuric acid treatment provides at least a 6 log reduction in the number of viable cells.

Example III

In this example a fermentation broth similar to that of Example I was used to show the affect of the pH adjustment on the cell kill. Also, in this example the amount of organic acid salt added was intentionally reduced below the optimal amount to show the effect of altering the pH of the mixture. In the following, samples 1–5 were used as is and 6–10 had 2% acetate (as 4.53 g of sodium acetate per 100 ml) added before pH adjustment. The pH of samples 1–5 before adjustment was about 5.8 and of samples 6–10 about 6.0. The pH of all samples was then adjusted to the values shown below, except for sample 4 which was not adjusted and which served as control sample of the broth. The pH was adjusted in each sample with $H_2SO_4$ or $NH_4OH$ to obtain the pH indicated.

| Sample | pH After Adjustment |
|--------|---------------------|
| 1 | 2.5 |
| 2 | 3.74 |
| 3 | 4.70 |
| 4 | 5.86 (no adjustment) |
| 5 | 6.7 |
| 6 | 2.79 |
| 7 | 3.76 |
| 8 | 4.76 |
| 9 | 5.6 |
| 10 | 6.8 |

All samples were stored on ice for 4 hours then the pH adjusted to 5.5 for plating on CMA plates with antibiotics. The plates were incubated at 37° C. for 7 days. The test results were as follows:

| Sample | $10^{-5}$ | $10^{-4}$ | $10^{-3}$ | $10^{-2}$ | 0.1 ml | 1 ml |
|--------|-----------|-----------|-----------|-----------|--------|------|
| 1 | 0 | 2 | 7 | 55 | TNTC | TNTC |
| 2 | 0 | 5 | 128 | TNTC | TNTC | TNTC |
| 3 | 1 | 47 | TNTC | TNTC | TNTC | TNTC |
| 4 | 3 | 64 | TNTC | TNTC | TNTC | TNTC |
| 5 | 3 | 66 | TNTC | TNTC | TNTC | TNTC |
| 6 | 0 | 0 | 0 | 0 | 2 | 62 |
| 7 | 0 | 1 | 2 | 37 | TNTC | TNTC |
| 8 | 0 | 1 | 3 | 56 | TNTC | TNTC |
| 9 | 3 | 35 | TNTC | TNTC | TNTC | TNTC |
| 10 | 3 | 34 | TNTC | TNTC | TNTC | TNTC |

This example illustrates the importance of adjusting the pH of the mixture to a value at or preferably below the $pK_a$ of the organic acid used. This example further illustrates that the addition of sodium acetate to the mixture and the adjustment of the pH of the mixture to 2.79 resulted in at least a 4 log reduction in the number of viable cells. A more complete cell kill would be obtained at the lower pH ranges if higher amounts of sodium acetate were used, such as 4%. However, the lower level of acetate was used in this example so the effect of the pH could be seen.

Example IV

This example illustrates the use of the present invention to kill yeast cells. For this example a yeast known as *Saccharomyces cerevisiae* was grown on a standard "YM" medium, available from Difco (Detroit, Mich.), at 250 rpm for 24 hrs at 37° C. As in Example 3 above, 10 samples were taken, samples 6–10 treated with 2% acetate (as sodium acetate), the pH adjusted to the value shown below, incubated for 4 hours and then plated.

| Sample | pH After Adjustment |
|--------|---------------------|
| 1 | 2.55 |
| 2 | 3.63 |
| 3 | 4.40 |
| 4 | 5.78 |
| 5 | 6.84 |
| 6 | 2.8 |
| 7 | 3.6 |
| 8 | 4.72 |
| 9 | 5.68 |
| 10 | 6.75 |

Test results:

| Sample | $10^{-5}$ | $10^{-6}$ | $10^{-7}$ | $10^{-8}$ | CFU/ml ($\times 10^7$) |
|--------|-----------|-----------|-----------|-----------|------------------------|
| 1 | TNTC | 42/41 | 7/2 | 1/3 | 4.2 |
| 2 | TNTC | 50/45 | 4/5 | 0/0 | 4.7 |
| 3 | TNTC | 49/48 | 3/5 | 2/1 | 4.9 |
| 4 | TNTC | 50/64 | 12/5 | 1/0 | 5.7 |
| 5 | TNTC | 43/54 | 5/9 | 1/1 | 4.9 |
| 6 | TNTC | 43/24 | 4/7 | 0/0 | 3.4 |
| 7 | TNTC | 32/34 | 5/8 | 1/1 | 3.3 |
| 8 | TNTC | 51/48 | 6/7 | 0/0 | 5.1 |
| 9 | TNTC | 56/58 | 4/5 | 1/2 | 5.7 |
| 10 | TNTC | 56/45 | 3/5 | 1/0 | 5.1 |

As can be concluded from the above, about 20% kill was obtained at pH 2.8, about 30% at pH 3.6, and no significant kill at pH 4.7, 5.7 or 6.75. While this example was run to determine the affect of pH on the effectiveness of the kill, it is apparent that a more effective kill would be achieved at higher levels of acetate, e.g., 4%. Also, as will be appreciated, it is more difficult to accurately quantify cell kill and culture growth of yeast than fungi, but this example demonstrates the usefulness of the present invention for yeast.

Having described this invention and illustrated particular embodiments of the invention, the scope of this invention is now defined by the claims that follow.

What is claimed is:

1. A method for killing cells without lysis in a fermentation culture containing an extracellularly produced enzyme and a fungus comprising the steps of:

(a) culturing the fungus to produce the fermentation culture containing the extracellularly produced enzyme and the fungus; and, in either order, (b) adjusting the pH of the fermentation culture to a value equal to or less than about 2 pH units below the $pK_a$ of a preselected organic acid having from 1 to 5 carbon atoms or a salt thereof with a mineral acid compatible with said extracellularly produced enzyme, and (c) adding from about 0.25 to 10% by weight of the preselected organic acid or salt thereof to the fermentation culture; then (d) recovering the extracellularly produced enzyme; wherein at least a four log decrease in the viable fungus in the fermentation culture is effected under conditions which are compatible with the extracellularly produced enzyme and the four log decrease in viable fungus is obtained without cell lysis.

2. A method according to claim 1 wherein the organic acid is formic acid, acetic acid, propionic acid or a salt thereof.

3. A method according to claim 1 wherein the mineral acid is sulfuric acid or hydrochloric acid.

4. A method according to claim 1 wherein the pH is adjusted before the organic acid or salt is added.

5. A method according to claim 1 wherein the organic acid or salt is added before the pH is adjusted.

6. The method according to claim 1 wherein the amount of preselected organic acid or salt thereof added to the culture is from about 0.5 to 10% by weight.

7. The method according to claim 1, wherein said organic acid has a $pK_a$ of less than 4.87.

* * * * *